United States Patent
Shinohara et al.

(10) Patent No.: US 11,304,635 B2
(45) Date of Patent: Apr. 19, 2022

(54) BIOLOGICAL MATERIAL MEASURING APPARATUS

(71) Applicant: Mitsubishi Electric Corporation, Chiyoda-ku (JP)

(72) Inventors: Kosuke Shinohara, Chiyoda-ku (JP); Kentaro Enoki, Chiyoda-ku (JP); Koichi Akiyama, Chiyoda-ku (JP); Shimpei Ogawa, Chiyoda-ku (JP); Daisuke Fujisawa, Chiyoda-ku (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 439 days.

(21) Appl. No.: 16/341,501

(22) PCT Filed: Nov. 22, 2017

(86) PCT No.: PCT/JP2017/042023
§ 371 (c)(1),
(2) Date: Apr. 12, 2019

(87) PCT Pub. No.: WO2018/123369
PCT Pub. Date: Jul. 5, 2018

(65) Prior Publication Data
US 2019/0307370 A1  Oct. 10, 2019

(30) Foreign Application Priority Data
Dec. 26, 2016  (JP) .............................. JP2016-251323

(51) Int. Cl.
A61B 5/1455  (2006.01)
A61B 5/00  (2006.01)
(Continued)

(52) U.S. Cl.
CPC .......... *A61B 5/1455* (2013.01); *A61B 5/0075* (2013.01); *A61B 5/14532* (2013.01);
(Continued)

(58) Field of Classification Search
CPC ... A61B 5/683; A61B 5/1455; A61B 5/14532; A61B 5/0075; A61B 5/7203;
(Continued)

(56) References Cited

U.S. PATENT DOCUMENTS

2004/0199060 A1  10/2004  Oshima et al.
2009/0059226 A1  3/2009  Kajiki et al.
2015/0265190 A1  9/2015  Ikebe

FOREIGN PATENT DOCUMENTS

CN  1536347 A  10/2004
DE  602004003414 T2  9/2007
(Continued)

OTHER PUBLICATIONS

Office Action dated Aug. 12, 2021, in corresponding German patent Application No. 112017006565.8, 12 pages.
(Continued)

*Primary Examiner* — Chu Chuan Liu
(74) *Attorney, Agent, or Firm* — Xsensus LLP

(57) ABSTRACT

A controller corrects a spectrum S (λ) detected at a wavelength λ of signal light to S' (λ) in accordance with expressions below: $I(\lambda)=(I2-I1)\times(\lambda-\lambda1)/(\lambda2-\lambda1)-I1$, and $S'(\lambda)=S(\lambda)-I(\lambda)$, where I1 is the intensity of infrared light detected at a wavelength λ1 of reference light and I2 is the intensity of infrared light detected at a wavelength λ2 of correction light.

20 Claims, 9 Drawing Sheets

(51) Int. Cl.
  *A61B 5/145* (2006.01)
  *G01N 21/359* (2014.01)
  *G01N 21/49* (2006.01)

(52) U.S. Cl.
  CPC ............ *A61B 5/683* (2013.01); *A61B 5/7203* (2013.01); *G01N 21/359* (2013.01); *G01N 21/49* (2013.01); *G01N 2201/1056* (2013.01)

(58) Field of Classification Search
  CPC . A61B 5/145; A61B 5/14542; A61B 5/14507; A61B 5/14546; A61B 5/14551; A61B 5/14552
  See application file for complete search history.

(56) References Cited

FOREIGN PATENT DOCUMENTS

| | | |
|---|---|---|
| EP | 1464273 A1 | 10/2004 |
| JP | 2004-340797 A | 12/2004 |
| JP | 2009-75073 A | 4/2009 |
| JP | 2015-173935 A | 10/2015 |
| JP | 2017-140159 A | 8/2017 |

OTHER PUBLICATIONS

International Search Report dated Feb. 20, 2018, in PCT/JP2017/042023 filed on Nov. 22, 2017.
Office Action dated May 31, 2021 in Chinese Patent Application No. 201780075247.1, 14 pages.

BIOLOGICAL MATERIAL MEASURING APPARATUS

TECHNICAL FIELD

The present invention relates to biological material measuring apparatuses, and more particularly, to a biological material measuring apparatus that uses infrared light to measure a biological material such as sugar in a living body.

BACKGROUND ART

A conventional invasive sensor draws blood with a needle and analyzes a component of a material in a living body. In particular, for blood sugar level sensors commonly used, a non-invasive type is desired to alleviate patient's pain caused by puncture. Although one type of non-invasive blood sugar level sensor using infrared light is capable of directly detecting a fingerprint spectrum of sugar, infrared light cannot reach a deep portion from a skin surface because infrared light is absorbed well by water. Under the circumstances, such a technique is demanded that detects a blood sugar level stably with high accuracy even when absorption by sugar in a living body is little.

In response to such a demand, for example, the apparatus described in PTL 1 has an SN ratio improved through a measurement using an attenuated total reflection (ATR) prism. The infrared light propagating through the ATR prism repeats total reflection at an interface between a measurement skin and the ATR prism. Evanescent light is generated at the interface at which total reflection occurs, and then penetrates the measurement skin. Since the evanescent light is absorbed and scattered by water, sugar, and any other biological material, the intensity of the infrared light propagating through the ATR prism attenuates. Thus, the intensity of propagating infrared light attenuates more with a larger number of repetitions of total reflection.

CITATION LIST

Patent Literature

PTL 1: Japanese Patent Laying-Open No. 2015-173935

SUMMARY OF INVENTION

Technical Problem

According to PTL 1, measurements are performed only near the absorption wavelength of glucose, and a correction reflecting a measurement error resulting from scattering by a living body is not made.

An object of the present invention is therefore to provide a biological material measuring apparatus that corrects detected infrared light while reflecting a measurement error resulting from scattering by a living body.

Solution to Problem

A biological material measuring apparatus of the present invention includes an infrared light source, an ATR prism, an infrared photodetector, and a controller. The infrared light source is configured to radiate infrared light including signal light, reference light, and correction light. The ATR prism is adherable to a living body surface. The infrared photodetector is configured to detect infrared light emitted from the ATR prism. The controller is configured to correct a spectrum S ($\lambda$) detected at a wavelength $\lambda$ of the signal light to S' ($\lambda$) in accordance with expressions (A1) and (A2) below:

$$I(\lambda)=(I2-I1)\times(\lambda-\lambda1)/(\lambda2-\lambda1)-I1 \quad (B1)$$

$$S'(\lambda)=S(\lambda)-I(\lambda) \quad (B2)$$

where I1 is the intensity of infrared light detected at a wavelength $\lambda1$ of the reference light and I2 is the intensity of infrared light detected at a wavelength $\lambda2$ of the correction light.

Advantageous Effects of Invention

In the present invention, the controller corrects spectrum S ($\lambda$) detected at wavelength $\lambda$ of the signal light to S' ($\lambda$) in accordance with expressions (B1) and (B2), where I1 is the intensity of the infrared light detected at wavelength $\lambda1$ of the reference light and I2 is the intensity of the infrared light detected at wavelength $\lambda2$ of the correction light. This corrects the detected infrared light in consideration of a measurement error attributable to scattering by a living body, enabling higher-accuracy measurement of a biological material.

DESCRIPTION OF EMBODIMENTS

Embodiments of the present invention will now be described with reference to the drawings.

Embodiment 1

Although description will be given below by taking a blood sugar level as an example biological material to be measured, a measuring apparatus of the present embodiment is applicable to measurement of a blood sugar level, as well as measurement of any other biological material.

Figure 1:
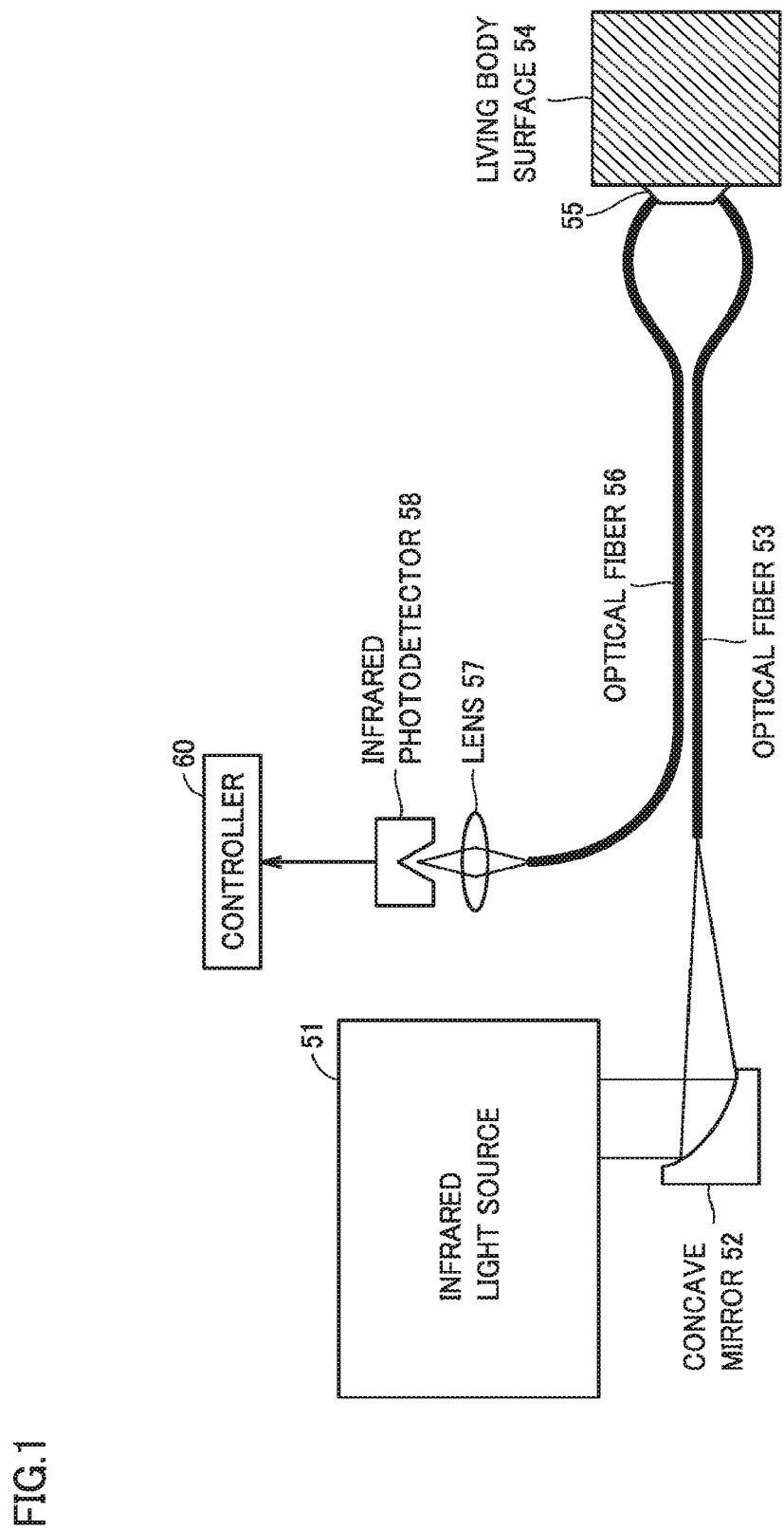
FIG. 1 shows a blood sugar level measuring apparatus of Embodiment 1.

FIG. 1 shows a blood sugar level measuring apparatus of Embodiment 1.

This blood sugar level measuring apparatus includes an infrared light source 51, a concave mirror 52, an optical fiber 53, an ATR prism 55, an optical fiber 56, a lens 57, an infrared photodetector 58, and a controller 60.

Infrared light source 51 is formed of, for example, a Fourier infrared spectrometer or wavelength tunable laser. The infrared light radiated from infrared light source 51 includes signal light, reference light with a wavelength λ1, and correction light with a wavelength λ2.

Concave mirror 52 collects infrared light emitted from infrared light source 51 and sends it to optical fiber 53.

Optical fiber 53 transmits infrared light. The tip of optical fiber 53 is connected to ATR prism 55.

Figure 2:
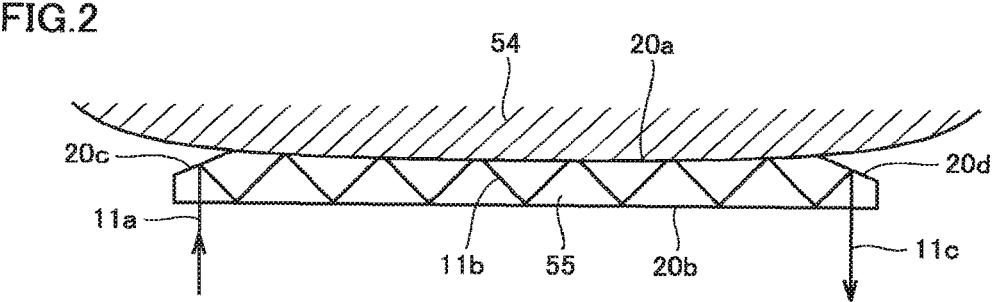
FIG. 2 shows an ATR prism 55.

ATR prism 55 is adherable to a living body surface 54. FIG. 2 shows ATR prism 55.

Incoming infrared light 11a emitted from optical fiber 53 is reflected off an end face 20c of ATR prism 55 and then turns into propagating infrared light 11b. Propagating infrared light 11b passes through ATR prism 55 being in contact with living body surface 54 while repeating total reflection off end faces 20a and 20b of ATR prism 55. Propagating infrared light 11b that has passed through ATR prism 55 is reflected off an end face 20d of ATR prism 55 and then turns into radiated infrared light 11c. Radiated infrared light 11c is transmitted to optical fiber 53.

One end of optical fiber 56 is connected to ATR prism 55 and receives infrared light emitted from ATR prism 55. Optical fiber 56 transmits infrared light. The other end of optical fiber 56 is connected to lens 57.

The infrared light emitted from optical fiber 56 is sent to infrared photodetector 58 through lens 57.

Infrared photodetector 58 detects infrared light that is emitted from ATR prism 55 and enters infrared photodetector 58 through optical fiber 56 and lens 57.

Figure 3:
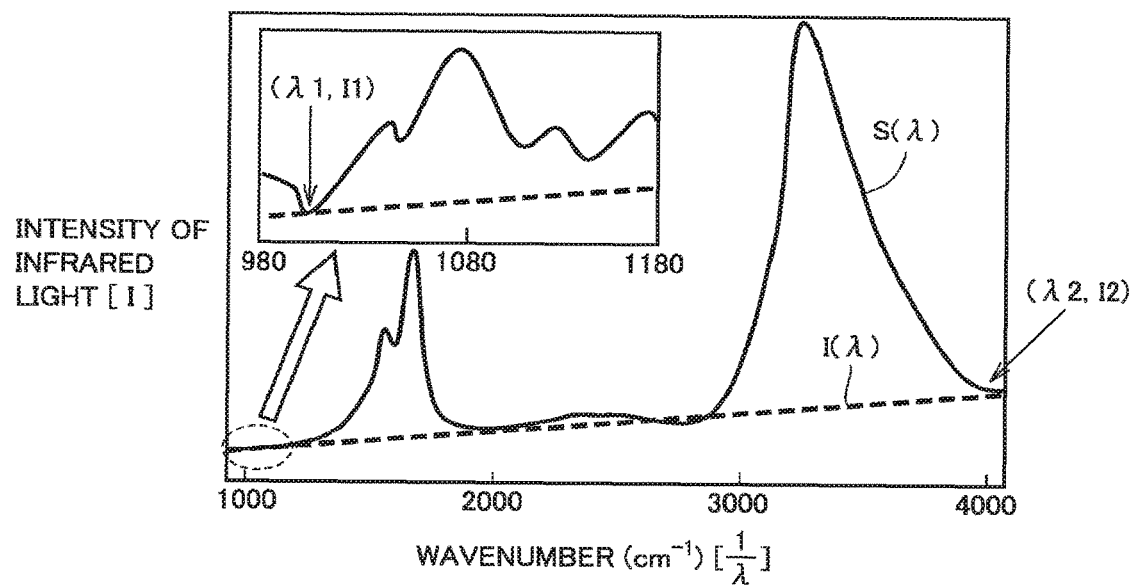
FIG. 3 shows an infrared spectrum measured by an infrared photodetector 58 in Embodiment 1.

FIG. 3 shows an infrared spectrum measured by infrared photodetector 58 in Embodiment 1.

Noise resulting from measurements and a living body is present in the infrared spectrum shown in FIG. 3. For example, noise may be caused by light absorption by a material other than glucose in a living body, a pressing pressure and a contact angle of ATR prism 55 with respect to a living body, and instabilities of a light scattering optical system in the living body.

In order to eliminate such noise, controller 60 corrects an infrared spectrum S (λ) detected at a wavelength λ, of signal light to S' (λ) in accordance with expressions below:

$$I(\lambda)=(I2-I1)\times(\lambda-\lambda1)/(\lambda2-\lambda1)-I1 \quad (1)$$

$$S'(\lambda)=S(\lambda)-I(\lambda) \quad (2)$$

where I1 is the intensity of the infrared light detected at wavelength λ1 of the reference light, and I2 is the intensity of the infrared light detected at wavelength λ2 of the correction light.

Reference light is used as a background, and accordingly, wavelength λ1 of the reference light is a wavelength at which absorption by a biological material to be measured is relatively large. Desirably, wavelength λ1 of the reference light is near the absorption peak of glucose and is not affected by absorption by glucose. For example, wavelength λ1 of the reference light is desirably a wavelength that is in the range of 8.0 to 10 μm and is not affected by absorption by glucose.

In order to eliminate an effect of light scattering in a living body, wavelength λ2 of the correction light is a wavelength at which absorption by a biological material to be measured is relatively small. Wavelength λ2 of the correction light is desirably a wavelength in an infrared region. For example, wavelength λ2 of the correction light is desirably 0.8 to 2.5 μm at which absorption by water is small.

Embodiment 2

Figure 4:
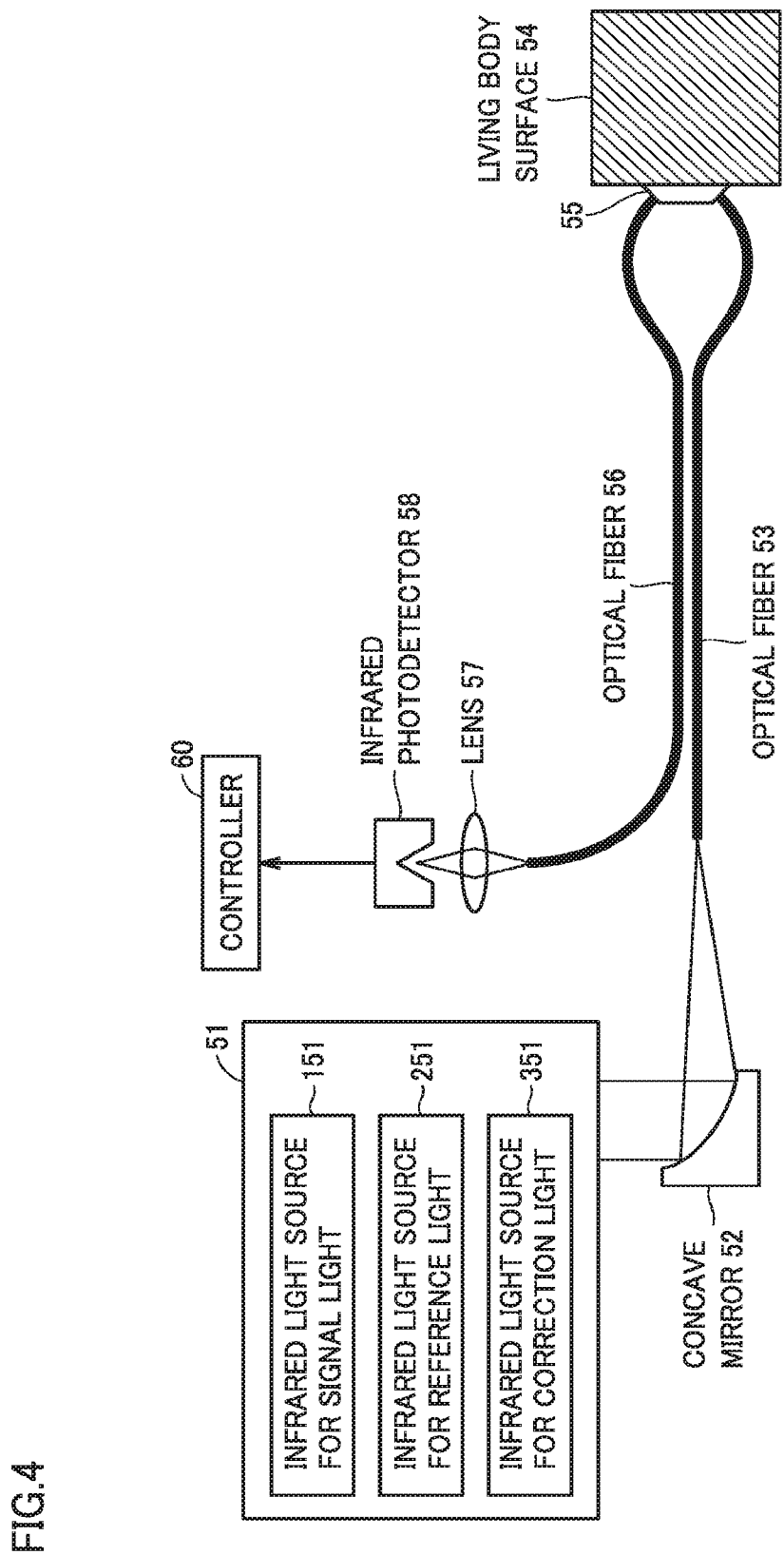
FIG. 4 shows a blood sugar level measuring apparatus of Embodiment 2.

FIG. 4 shows a blood sugar level measuring apparatus of Embodiment 2.

The blood sugar level measuring apparatus of Embodiment 2 differs from the blood sugar level measuring apparatus of Embodiment 1 in infrared light source 51 and controller 60.

Infrared light source 51 includes an infrared light source for signal light 151 that radiates signal light used in calculation of a blood sugar level, an infrared light source for reference light 251 that radiates reference light used as a background, and an infrared light source for correction light 351 that radiates correction light.

Infrared light source for signal light 151, infrared light source for reference light 251, and infrared light source for correction light 351 radiate light with a specific wavelength.

Infrared light source for signal light 151 is a quantum cascade laser that radiates signal light with a single wavelength λ1. Infrared light source for reference light 251 is a quantum cascade laser that radiates reference light with a single wavelength λ2. The quantum cascade laser can oscillate in a mid infrared region and is compact and is high in output.

Infrared light source for correction light 351 is a semiconductor laser that radiates correction light with a single wavelength λ3. The semiconductor laser is used in optical communications and is inexpensive.

Figure 5:
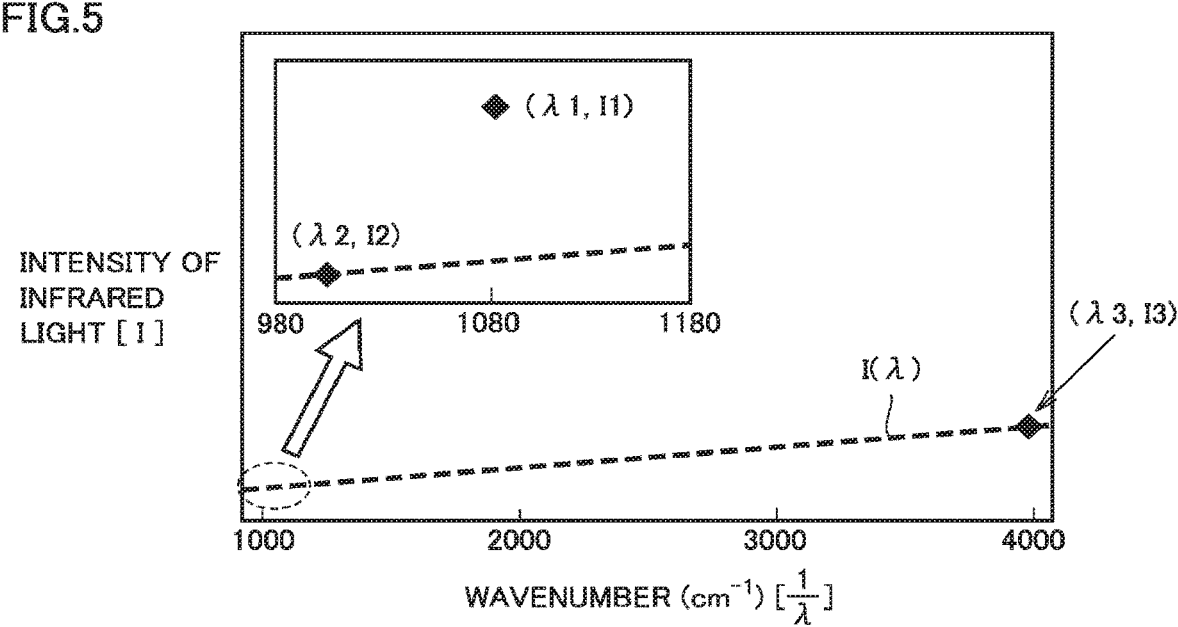
FIG. 5 shows infrared intensities measured by infrared photodetector 58 in Embodiment 2.

FIG. 5 shows infrared intensities measured by infrared photodetector 58 in Embodiment 2.

As shown in FIG. 5, the use of a laser light source that radiates light with a specific wavelength results in an infrared light intensity, not an infrared spectrum.

In order to eliminate such noise, controller 60 corrects an intensity I1 of the infrared light detected at wavelength λ1 of the signal light to I1' in accordance with expressions below:

$$I(\lambda)=(I3-I2)\times(\lambda-\lambda2)/(\lambda3-\lambda2)-I2 \quad (3)$$

$$I1'=I1-I(\lambda1) \quad (4)$$

where I2 is the intensity of the infrared light detected at wavelength λ2 of the reference light, and I3 is the intensity of the infrared light detected at wavelength λ3 of the correction light.

Herein, wavelength λ1 of the signal light is a wavelength at which absorption by a biological material to be measured is relatively large. Wavelength λ1 of the signal light is desirably a wavelength that approximately matches any absorption peak of glucose. For example, wavelength λ1 is desirably a wavelength that is in the range of 8.0 to 10 μm and approximately matches any absorption peak of glucose.

The reference light is used as a background, and thus, wavelength λ2 of the reference light is a wavelength at which absorption by a biological material to be measured is relatively large. Wavelength λ2 of the reference light is desirably a wavelength that is near the absorption peak of glucose and is not affected by absorption of glucose. For example, wavelength λ2 of the reference light is desirably a wavelength that is in the range of 8.0 to 10 μm and is not affected by absorption of glucose.

In order to eliminate an effect of light scattering in a living body, wavelength λ3 of the correction light is a wavelength at which absorption by a biological material to be measured is relatively small. Wavelength λ3 of the correction light is desirably a wavelength in a near infrared region. For example, wavelength λ3 of the correction light is desirably 0.8 to 2.5 μm at which absorption by water is small.

Modification 1 of Embodiment 2

Infrared light source for signal light 151 and infrared light source for reference light 251 may be a plurality of quantum cascade lasers that oscillate at wavelengths approximately matching a plurality of absorption peaks. This enables measurement of a blood sugar level using a plurality of wavelengths, further improving accuracy.

Alternatively, infrared light source for signal light 151 and infrared light source for reference light 251 may be a wavelength integrated device including integration of a plurality of quantum cascade lasers that radiate infrared light with a single wavelength. The use of a wavelength integrated device can miniaturize an apparatus and simplify assembly of an apparatus.

Modification 2 of Embodiment 2

Infrared light source 51 may be a quantum cascade laser that radiates laser at a wide band, a thermal light source of a type that flows current through a filament for heating, or a plasmon or metamaterial light source that has a periodic pattern provided in a heating portion. Infrared photodetector 58 may be configured to selectively detect a specific wavelength. The thermal light source of the type that flows current through a filament for heating has a temperature controllable by an amount of current applied, and accordingly, radiates infrared rays at a wide band according to black body radiation. The plasmon or metamaterial light source that has a periodic pattern in a heating portion is a high-efficiency light source because its radiation wavelength range is defined by surface structure and accordingly has reduced unnecessary radiation.

Embodiment 3

Figure 6:
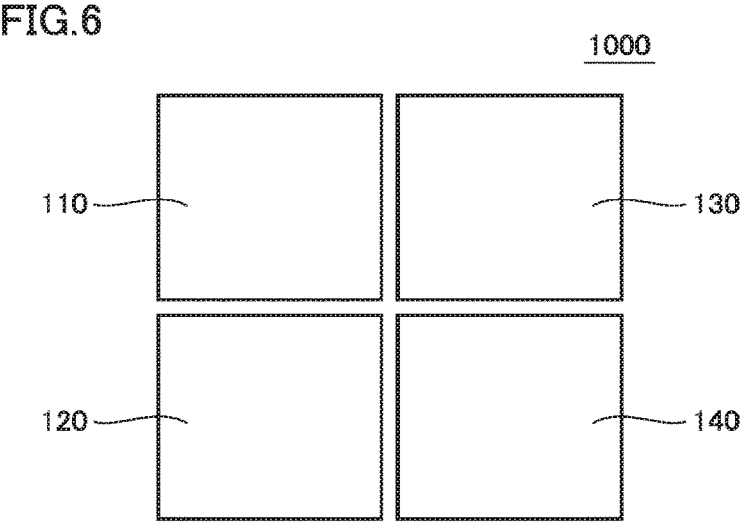
FIG. 6 is a schematic view of a sensor array 1000 of an infrared photodetector 58 of Embodiment 3.

FIG. 6 is a schematic view of a sensor array 1000 of an infrared photodetector 58 of Embodiment 3. Sensor array 1000 is formed of non-cooling infrared sensors (hereinafter, also referred to as sensor pixels) 110, 120, 130, and 140 each detecting light having a different wavelength.

Sensor pixels 110, 120, 130, and 140 each include, for example, a wavelength-selective absorber using a plasmon resonance on the surface of a light receiving portion. The wavelength-selective absorber detects infrared light with the selected wavelength. The use of infrared photodetector 58 including an array of non-cooling infrared sensors which detect only the infrared light having the selected wavelength allows simultaneous measurements of a plurality of wavelengths, enabling a measurement in a short period of time.

As described below, the use of a plasmon resonance eliminates the need for a spectral filter, simplifying an apparatus configuration, which leads to lower cost. Although wavelength selectivity decreases due to the thermal radiation of a filter per se in an infrared wavelength range, the use of plasmon structure in the light receiving portion improves wavelength selectivity. This leads to higher sensitivity for detecting a trace amount of component, such as analysis of a blood sugar level.

In one example in which the wavelengths of signal light are λA and λB, the wavelength of reference light is λC, and the wavelength of correction light is λD, sensor pixels 110, 120, 130, and 140 of infrared photodetector 58 detect infrared light with a wavelength λA, infrared light with a wavelength λB, infrared light with a wavelength λC, and infrared light with a wavelength λD. The infrared photodetector for a wavelength of correction light may be an inexpensive photodetector for use in optical communications.

At least one of wavelengths λA and λB corresponds to the wavelength of a biological material to be measured.

Although the infrared rays radiated from an external background and a human body may enter infrared photodetector 58, setting wavelengths λA, λB, and λC to values extremely close to each other makes the effects of the infrared rays radiated from a background and a human body almost equal to each other, thus minimizing the effects of noise.

In order to eliminate such noise, radiated infrared light may be chopped at a specific frequency using a chopper. Infrared light source 51 itself can be pulse-driven, and infrared light can be chopped using the frequency thereof to increase detection sensitivity. The output signals from sensor pixels 110, 120, 130, and 140 may be subjected to Fourier transform at a chopping frequency to obtain an output with noise reduced.

It suffices that a sensor pixel may be added in order to increase wavelengths to be detected. When a detection wavelength can be adjusted by controlling only the surface periodic structure of a sensor pixel, as many wavelengths as the pixels formed into an array can be detected.

A specific example of infrared photodetector 58 will now be described.

The models of non-cooling infrared sensors (thermal infrared sensors) for use in the sensor pixels of infrared photodetector 58 include pyroelectric sensors, bolometers, thermopiles, and silicon on insulator (SOI) diodes. Even for different models, a plasmon resonance can be used for a light receiving portion of the sensor, that is, an absorber to enable the selection of wavelengths. The present embodiment can thus use any model as infrared photodetector 58 irrespective of the model of a non-cooling infrared sensor.

Embodiment 4

Figure 7:
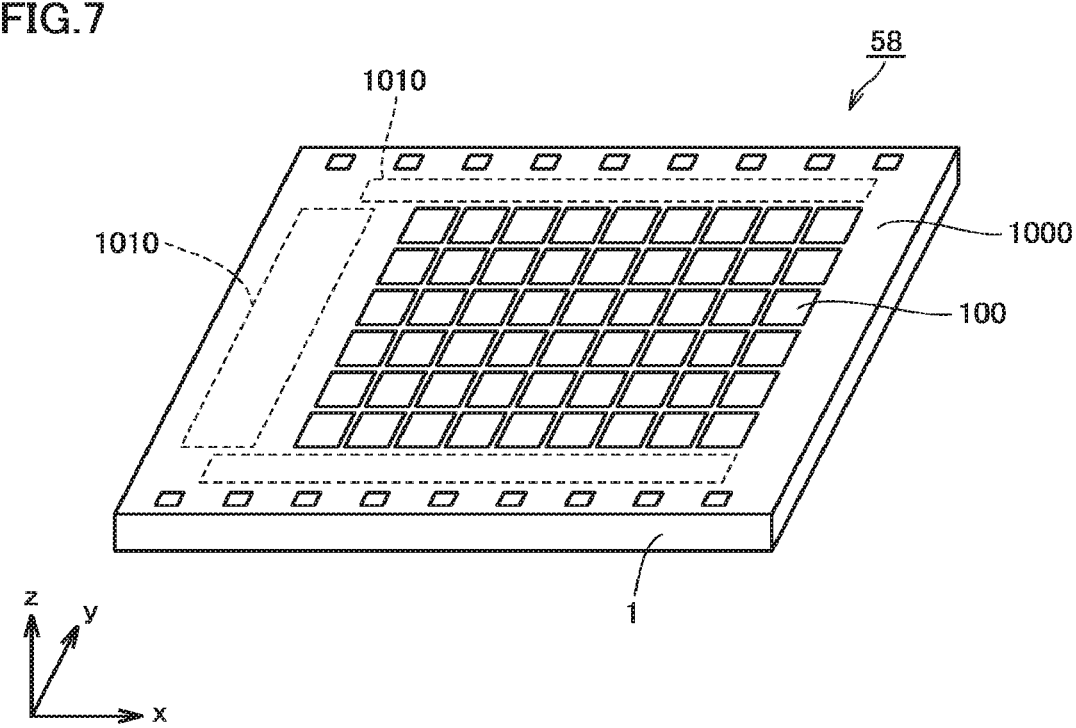
FIG. 7 shows a configuration of an infrared photodetector 58 of Embodiment 4.

FIG. 7 shows a configuration of an infrared photodetector 58 of Embodiment 4.

Infrared photodetector 58 is an integrated wavelength-selective infrared sensor. Infrared photodetector 58 includes a sensor array 1000 and a detection circuit 1010.

Sensor array 1000 includes 9×6 pixels (semiconductor optical devices) 100 arranged in row and columns. On substrate 1, 9×6 semiconductor optical devices 100 are arranged in matrix (in array) in the X-axis and Y-axis directions. Light enters from the direction parallel to the Z-axis. That is to say, infrared photodetector 58 perpendicularly receives infrared light emitted from ATR prism 55.

Detection circuit 1010 is provided around sensor array 1000. Detection circuit 1010 processes a signal detected by semiconductor optical device 100 to detect an image. When the detected wavelengths are fewer, detection circuit 1010 is not required to detect an image and is merely required to detect an output from each device.

Figure 8:
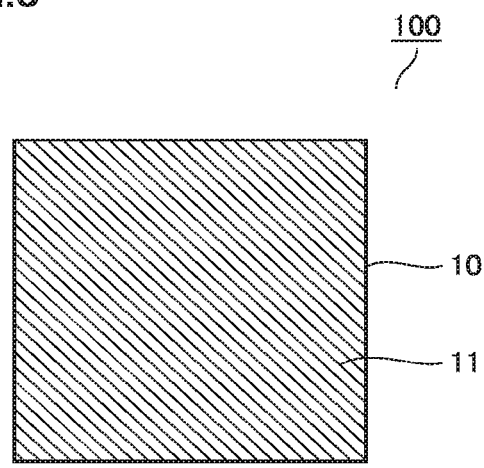
FIG. 8 is a top view of a semiconductor optical device 100 of Embodiment 4.

Description will now be given by taking a thermal infrared sensor as an example of semiconductor optical device 100. FIG. 8 is a top view of semiconductor optical device 100 of Embodiment 4. As shown in FIG. 8, semiconductor optical device 100 includes absorber 10.

Figure 9:
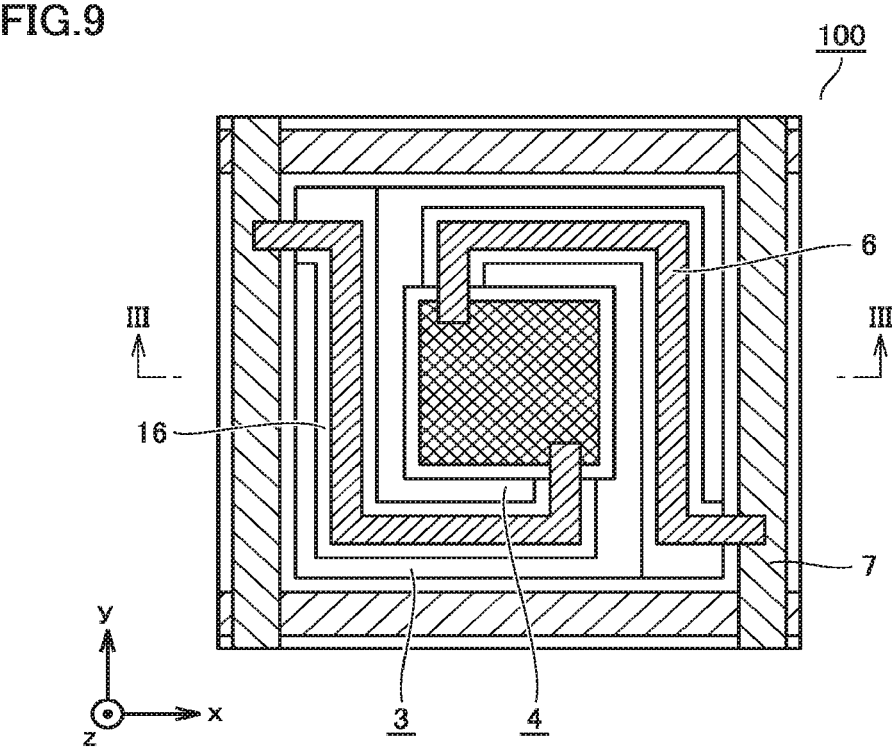
FIG. 9 is a top view of semiconductor optical device 100 of Embodiment 4 excluding an absorber 10.
Figure 10:
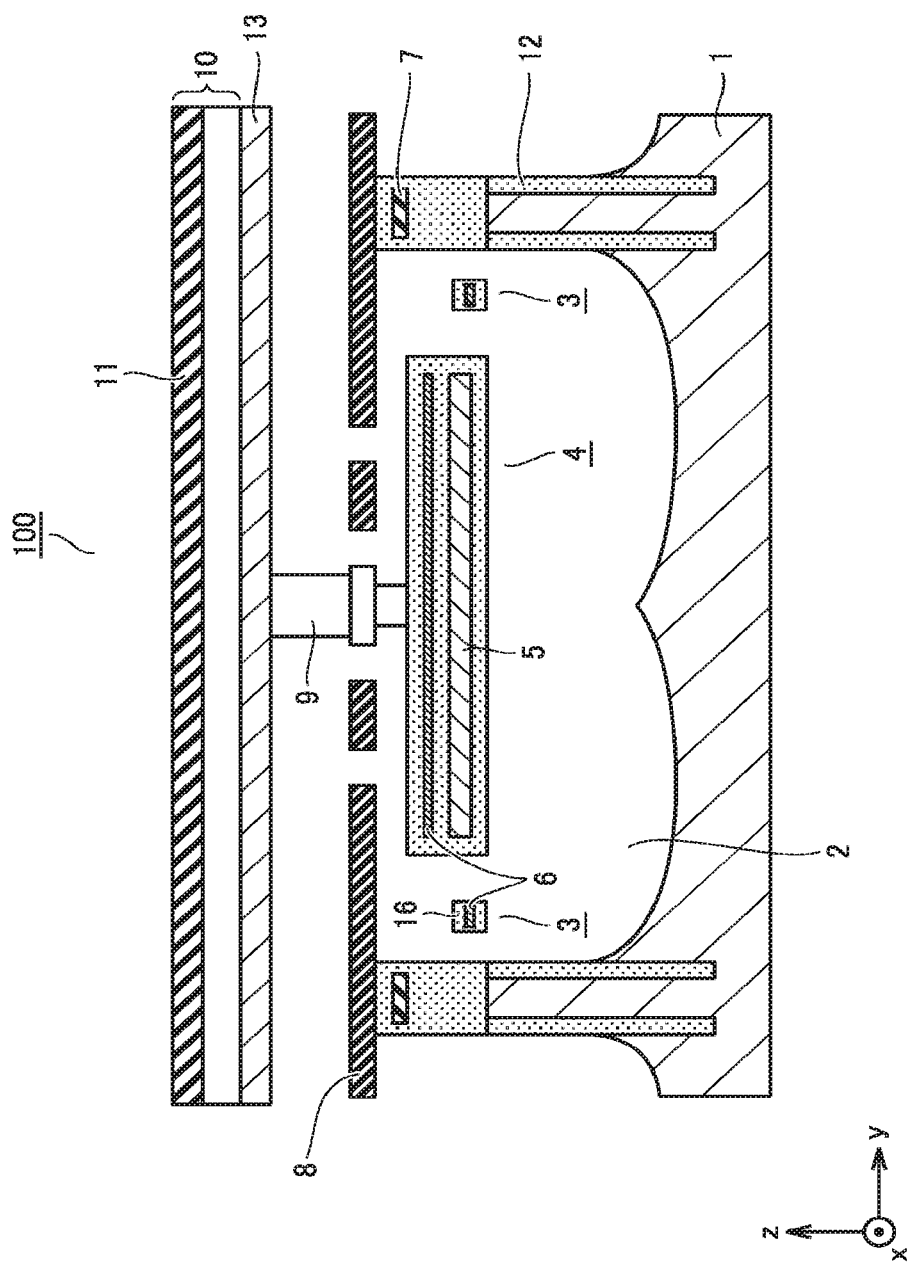
FIG. 10 is a sectional view of semiconductor optical device 100 of FIG. 9, as seen in the III-III direction.
Figure 11:
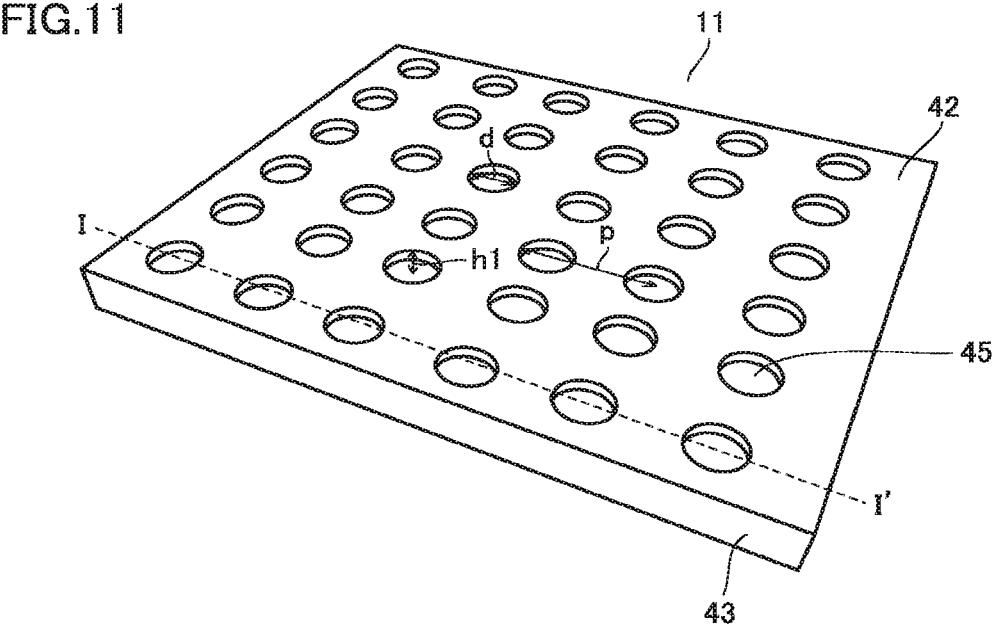
FIG. 11 shows an absorber 10 of semiconductor optical device 100 of Embodiment 4.

FIG. 9 is a top view of semiconductor optical device 100 of Embodiment 4 excluding absorber 10. FIG. 9 does not show a protective film or a reflection film on a wire for clarification. FIG. 10 is a sectional view (including absorber 10 and the like) of semiconductor optical device 100 of FIG. 9, as seen in the direction of FIG. 9. FIG. 11 shows absorber 10 of semiconductor optical device 100 of Embodiment 4.

As shown in FIGS. 7 to 11, semiconductor optical device 100 includes, for example, a substrate 1 made of silicon. A hollow 2 is provided in substrate 1. A temperature detection unit 4 that detects temperatures is disposed above hollow 2. Temperature detection unit 4 is supported by two support legs 3. As shown in FIG. 9, support leg 3 has a bridge shape bent in an L-shape as seen from above. Support leg 3 includes a thin metal wire 6 and a dielectric film 16 supporting thin metal wire 6.

Temperature detection unit 4 includes a detection film 5 and thin metal wire 6. Detection film 5 is formed of, for example, a diode containing crystal silicon. Thin metal wire 6 is also provided in support leg 3 and electrically connects an aluminum wire 7 and detection film 5, which are covered with an insulating film 12, to each other. Thin metal wire 6 is made of, for example, titanium alloy having a thickness of 100 μm. An electric signal output from detection film 5 is transmitted to aluminum wire 7 through thin metal wire 6 formed in support leg 3 and is extracted by detection circuit 1010 of FIG. 7. An electrical connection between thin metal wire 6 and detection film 5 and between thin metal wire 6 and aluminum wire 7 may be provided via a conductor (not shown) extending thereabove or therebelow if necessary.

Reflective film 8 that reflects infrared rays is disposed to cover hollow 2; however, it is disposed to cover at least part of support leg 3 with reflective film 8 and temperature detection unit 4 not being thermally connected to each other.

As shown in FIG. 10, a support pillar 9 is provided above temperature detection unit 4. Absorber 10 is supported on support pillar 9. That is to say, absorber 10 is connected to temperature detection unit 4 by support pillar 9. Since absorber 10 is thermally connected to temperature detection unit 4, a change in the temperature generated in absorber 10 is conveyed to temperature detection unit 4.

At the same time, absorber 10 is disposed above reflective film 8 while it is not thermally connected to reflective film 8. Absorber 10 extends laterally in a plate shape so as to cover at least part of reflective film 8. As seen from above, thus, only absorber 10 is viewed in semiconductor optical device 100 as shown in FIG. 8. Alternatively, absorber 10 may be formed directly on temperature detection unit 4.

In the present embodiment, wavelength selection structure 11 that selectively absorbs the light with a certain wavelength is provided in the surface of absorber 10 as shown in FIGS. 8 and 10. Also, an anti-absorption film 13 that prevents light absorption from the rear surface is provided on the rear surface of absorber 10, that is, on the support pillar 9 side. This configuration allows absorber 10 to selectively absorb light with a specific wavelength. Since wavelength selection structure 11 may absorb light, absorber 10 in the present embodiment includes wavelength selection structure 11.

Description will now be given of a case in which wavelength selection structure 11 is configured to use a surface plasmon. Providing a periodic structure made of metal in a light incidence surface causes a surface plasmon at a wavelength corresponding to a surface periodic structure, so that light is absorbed. Thus, the surface of absorber 10 can be made of metal to control the wavelength selectivity of absorber 10 by the wavelength of incident light, an angle of incidence, and a periodic structure of the metal surface.

In the present embodiment, a phenomenon in which free electrons inside a metal film make a contribution and the generation of a surface mode by a periodic structure are regarded as being synonymous with each other in terms of absorption, and they are merely referred to as a surface plasmon or a surface plasmon resonance, or merely as a resonance without differentiating therebetween. Although they may also be referred to as a pseudo-surface plasmon and a metamaterial, they are treated similarly as a phenomenon in terms of absorption. The configuration of the present embodiment is also effective for light with a wavelength in a wavelength region other than infrared light, for example, a visible region, a near infrared region, and a THz region.

As shown in FIG. 11, wavelength selection structure 11 that selectively increases the absorption of light with a certain wavelength, which is provided in the surface of absorber 10, includes a metal film 42, a main body 43, and recesses 45.

The type of metal film 42 provided in the surface of absorber 10, that is, in the outermost surface of semiconductor optical device 100 which is a light receiving portion, is selected from metals that cause a surface plasmon resonance, such as Au, Ag, Cu, Al, Ni, and Mo. Alternatively, the type of metal film 42 may be a material that causes a plasmon resonance, such as metallic nitrides including TiN, metallic borides, and metallic carbides. It suffices that metal film 42 in the surface of absorber 10 has such a thickness as not to allow incoming infrared light to pass therethrough. With such a film thickness, only a surface plasmon resonance on the surface of absorber 10 affects absorption and radiation of electromagnetic waves, and the material below metal film 42 does not optically affect absorption or the like.

A thickness (skin depth) $\delta 1$ of a skin effect is represented by expression below:

$$\delta 1 = (2/\mu\sigma\omega)^{1/2} \qquad (5)$$

where $\mu$ is a magnetic permeability of metal film 42, $\sigma$ is an electric conductivity of metal film 42, and $\omega$ is an angular frequency of incident light.

For example, when film thickness $\delta$ of metal film 42 in the surface of absorber 10 is at least twice $\delta 1$, that is, from about several tens of nanometers to about several hundreds of nanometers, a leak of incident light to below absorber 10 can be made sufficiently small.

For example, in comparison of heat capacity between gold and oxide silicon ($SiO_2$), oxide silicon has a smaller heat capacity. An absorber formed of main body 43 made of oxide silicon and the surface of metal film 42 made of gold can have a smaller heat capacity than an absorber made of gold alone, and accordingly, can have a higher response.

A method of manufacturing absorber 10 will now be described.

A periodic structure is formed on the front surface side of main body 43 formed of a dielectric or semiconductor by photolithography and dry etching, and then, metal film 42 is formed by sputtering or the like. Similarly for the rear surface, subsequently, a periodic structure is produced, and then, metal film 42 is formed.

Since the diameter of recess 45 is as small as about several micrometers, a manufacturing step is more simplified by forming metal film 42 after etching main body 43 to form recesses than by directly etching metal film 42 to form recesses.

Since an expensive material such as Au or Ag is used for metal film 42, the use of main body 43 of dielectric or semiconductor can reduce the amount of metal used for reduced cost.

The characteristics of absorber 10 will now be described with reference to FIG. 11. Cylindrical recesses 45 each having a diameter d of 4 µm and a depth h of 1.5 µm are arranged in tetragonal lattice in periods p of 8 µm in a surface of semiconductor optical device 100 that is a light receiving portion. In this case, an absorption wavelength is about 8 µm. Alternatively, cylindrical recesses 45 each having a diameter d of 4 µm and a depth h of 1.5 µm are arranged in tetragonal lattice in periods p of 8.5 µm. In this case, an absorption wavelength is almost about 8.5 µm.

A relationship between the absorption wavelength and radiation wavelength of incident light and the period of recess 45 is almost identical among the arrangements in, for example, tetragonal lattice and triangular lattice as long as they have a two-dimensional periodic structure, and an absorption wavelength and a radiation wavelength are determined by the period of recess 45. Considering reciprocal vectors of the periodic structure, theoretically, the absorption and radiation wavelengths are almost identical to the period in the arrangement in tetragonal lattice, whereas the absorption and radiation wavelengths are a period $\times\sqrt{3}/2$ in the arrangement in triangular lattice. In actuality, however, the absorption and radiation wavelengths vary slightly depending on diameter d of recess 45. It is thus conceivable that incident light may be absorbed or radiated at a wavelength almost identical to a period in both the periodic structures.

The wavelength of infrared light to be absorbed can thus be controlled by the period of recess 45. The period of recess 45 is determined such that a wavelength at which infrared light is absorbed by absorber 10 matches the absorption wavelength of a biological material to be measured.

Generally, diameter d of recess 45 is desirably not less than a half of period p. If diameter d of recess 45 is smaller than a half of period p, a resonance effect tends to be smaller to reduce an absorptivity. However, since a resonance is a three-dimensional resonance in recess 45, a sufficient absorption may be achieved even when diameter d is smaller than a half of period p. The value of diameter d with respect to period p is accordingly designed individually as appropriate. What is important is that an absorption wavelength is controlled mainly by period p. When diameter d is not less than a certain value with respect to period p, absorber 10 has sufficient absorption characteristics, providing ranges to design. Meanwhile, referring to a general expression of dispersion relation of a surface plasmon, the light to be absorbed is irrelevant to depth h of recess 45 and depends on period p alone. The absorption wavelength and radiation wavelength thus do not depend on depth h of recess 45 shown in FIG. 11.

Although the absorber having recesses 45 arranged periodically has been described above, similar effects can be achieved also with the structure having projections arranged periodically.

The absorption by absorber 10 having an irregular structure reaches its maximum in the case of normal incidence. When the angle of incidence on absorber 10 deviates from normal incidence, the absorption wavelength also changes. Infrared photodetector 58 is thus disposed such that infrared light is radiated perpendicularly to absorber 10.

Embodiment 5

Figure 12:
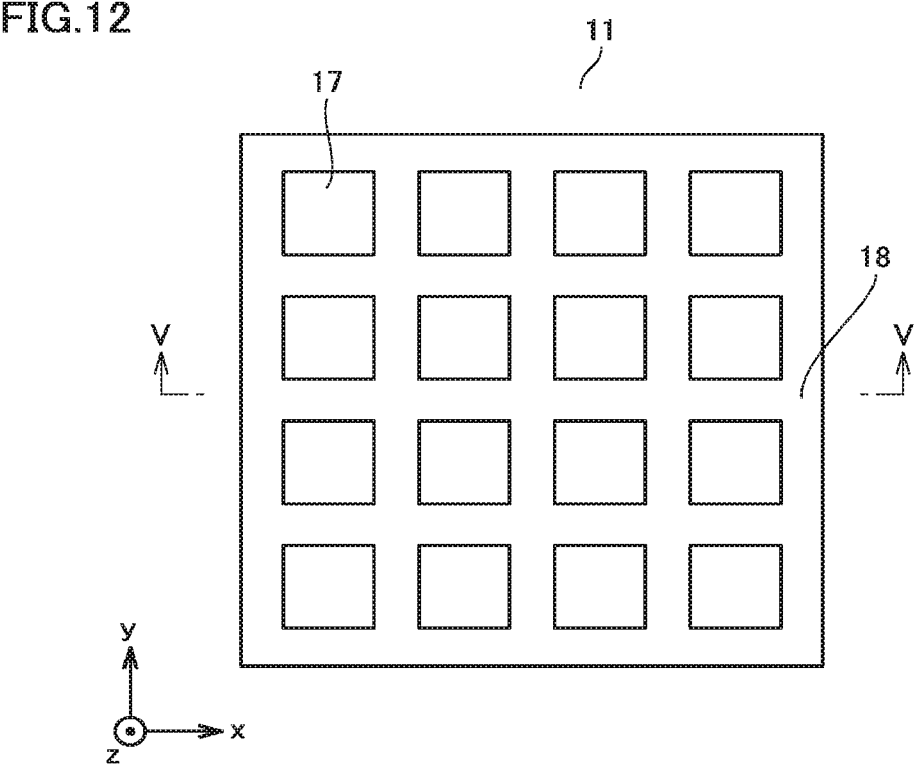
FIG. 12 is a top view of a wavelength selection structure 11 of Embodiment 5.
Figure 13:
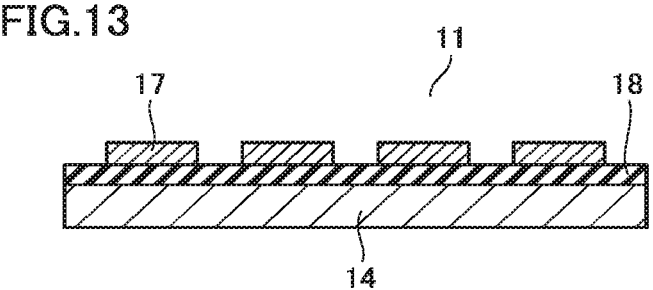
FIG. 13 is a sectional view of wavelength selection structure 11 of FIG. 12, as seen in the V-V direction.

FIG. 12 is a top view of a wavelength selection structure 11 of Embodiment 5. FIG. 13 is a sectional view of wavelength selection structure 11 of FIG. 12, as seen in the V-V direction.

Wavelength selection structure 11 includes a thin metal film 14, an insulating film 18 on thin metal film 14, and metal patches 17 on insulating film 18.

Thin metal film 14 is made of, for example, aluminum, gold, or the like.

Insulating film 18 is formed of, for example, oxide silicon. Insulating film 18 is formed of an insulator, a dielectric, or a semiconductor such as silicon or germanium. The selection of the material for insulating film 18 can control a wavelength to be detected, the number of wavelengths to be detected, and the band of a wavelength to be detected.

Metal patch 17 is formed of, for example, a metal such as gold, silver, or aluminum.

The wavelength at which a plasmon resonance occurs can be controlled by the size of metal patch 17 (the dimensions in the x and y directions of FIG. 12). Thus, changing the size of metal patch 17 allows the selection of an absorption wavelength. The size of a metal patch can accordingly be determined such that the wavelength absorbed by absorber 10 matches the absorption wavelength of a biological material to be measured. As shown in FIG. 12, in one example in which metal patch 17 has a square shape, the absorption wavelength is about 7.5 µm when the length of one side is 3 µm, and the absorption wavelength is about 8.8 µm when the length of one side is 3.5 µm. In this case, the periods of metal patches 17 are determined to be greater than the absorption wavelength of a biological material to be measured and greater than one side of metal patch 17. This allows the periods of metal patches 17 to cause almost no effects on the absorption wavelength.

The use of the absorber of the present embodiment can miniaturize pixels, reducing the area of infrared photodetector 58 when the pixels are formed into an array.

The absorption structure of wavelength selection structure 11 of the present embodiment has no independence on an angle of incidence, and the absorption wavelength does not change even when an angle of incidence is changed. Similarly, when metal patch 17 has a symmetrical shape or a two-dimensional periodic structure, the absorption structure has no polarization independence. Thus, a permissible range is extended for the angle at which infrared photodetector 58 is installed. For a mobile type, since a deviation of infrared photodetector 58 is feared, the use of the absorption structure of the present embodiment has a remarkable effect of good portability.

Although metal patches 17 are arranged in regular periods in matrix (two-dimensionally) in FIG. 12, they may be arranged one-dimensionally. Although polarization dependence occurs in this case, stray light can be eliminated by matching the direction of arrangement with the polarization of an infrared light source. An SN ratio can thus be improved, enabling higher-accuracy measurement of a blood sugar level.

Metal patch 17 may be replaced by a patch made of graphene other than metal. When metal patch 17 is made of graphene, a film thickness can be reduced down to one atomic layer. This reduces a thermal time constant, enabling a high-speed operation. Alternatively, metal patch 17 may be replaced by a material that causes a surface plasmon resonance as described above.

Insulating film 18 may be replaced by an insulator such as oxide silicon, a dielectric, or a semiconductor such as silicon or germanium. The selection of material can control a wavelength to be detected, the number of wavelengths to be detected, and the band of a wavelength to be detected.

It is to be understood that the embodiments disclosed herein are presented for the purpose of illustration and non-restrictive in every respect. It is therefore intended that the scope of the present invention is defined by claims, not only by the embodiments described above, and encompasses all modifications and variations equivalent in meaning and scope to the claims.

REFERENCE SIGNS LIST

1 substrate, 2 hollow, 3 support leg, 4 temperature detection unit, 5 detection film, 6 thin metal wire, 7 aluminum wire, 8 reflective film, 9 support film, 10 absorber, 11 wavelength selection structure, 11a incoming infrared light, 11b propagating infrared light, 11c radiated infrared light, 12 insulating film, 13 anti-absorption film, 14 thin metal film, 16 dielectric film, 17 metal patch, 18 insulating film, 20a, 20b, 20c, 20d ATR prism end face, 42 metal film, 43 main body, 45 recess, 51 infrared light source, 52 concave mirror, 53, 56 optical fiber, 54 living body surface, 55 ATR prism, 57 light receiving lens, 58 infrared photodetector, 100 semiconductor optical device, 110, 120, 130, 140 non-cooling infrared sensor, 1000 sensor array, 1010 detection circuit.

The invention claimed is:

1. A biological material measuring apparatus comprising:
an infrared light source configured to radiate infrared light including signal light, reference light, and correction light;
an ATR prism configured to adhere to a living body surface;
an infrared photodetector configured to detect infrared light emitted from the ATR prism; and
a controller configured to correct a spectrum or an intensity of the signal light based on an intensity of infrared light detected at a wavelength of the reference light and a wavelength of the correction light,
wherein:
the controller is configured to correct a spectrum $S(\lambda)$ detected at a wavelength $\lambda$ of the signal light to $S'(\lambda)$ in accordance with expressions (A1) and (A2) below $$I(\lambda)=(I2-I1)\times(\lambda-\lambda 1)/(\lambda 2-\lambda 1)-I1 \quad (A1)$$

$$S'(\lambda)=S(\lambda)-I(\lambda) \quad (A2)$$

where I1 is the intensity of infrared light detected at a wavelength $\lambda 1$ of the reference light and I2 is the intensity of infrared light detected at a wavelength $\lambda 2$ of the correction light.

2. The biological material measuring apparatus according to claim 1, wherein
the ATR prism has a first end face, a second end face, a third end face, and a fourth end face, and
the infrared light radiated from the infrared light source is incident on the first end face, and the infrared light that has been incident on the first end face passes through the ATR prism while repeating total reflection off the second end face and the third end face and is then emitted from the fourth end face.

3. The biological material measuring apparatus according to claim 1, wherein
the wavelength of the signal light and the wavelength of the reference light are wavelengths at which absorption by a biological material to be measured is relatively large, and
the wavelength of the correction light is a wavelength at which absorption by the biological material to be measured is relatively small.

4. The biological material measuring apparatus according to claim 3, wherein
the wavelength of the signal light and the wavelength of the reference light are 8.0 to 10 μm, and
the wavelength of the correction light is 0.8 to 2.5 μm.

5. The biological material measuring apparatus according to claim 3, wherein
the infrared light source includes
an infrared light source for the signal light configured to radiate the signal light, and
an infrared light source for the reference light configured to radiate the reference light, and
each of the infrared light source for signal light and the infrared light source for reference light is a quantum cascade laser configured to radiate infrared light with a single wavelength.

6. A biological material measuring apparatus comprising:
an infrared light source configured to radiate infrared light including signal light reference light, and correction light;
an ATR prism configured to adhere to a living body surface;
an infrared photodetector configured to detect infrared light emitted from the ATR prism; and
a controller configured to correct a spectrum or an intensity of the signal light based on an intensit of infrared light detected at a wavelength of the reference light and a wavelength of the correction light,
wherein:
the controller is configured to correct an intensity I1 of infrared light detected at a wavelength $\lambda 1$ of the signal light to I1' in accordance with expressions (A3) and (A4) below $$I(\lambda)=(I3-I2)\times(\lambda-\lambda 2)/(\lambda 3-\lambda 2)-I2 \quad (A3)$$

$$I1'=I1-I(\lambda 1) \quad (A4)$$

where I2 is the intensity of the infrared light detected at wavelength $\lambda 2$ of the reference light, and I3 is the intensity of the infrared light detected at wavelength $\lambda 3$ of correction light.

7. The biological material measuring apparatus according to claim 6, wherein
the ATR prism has a first end face, a second end face, a third end face, and a fourth end face, and
the infrared light radiated from the infrared light source is incident on the first end face, and the infrared light that has been incident on the first end face passes through the ATR prism while repeating total reflection off the second end face and the third end face and is then emitted from the fourth end face.

8. The biological material measuring apparatus according to claim 6, wherein
the wavelength of the signal light and the wavelength of the reference light are wavelengths at which absorption by a biological material to be measured is relatively large, and
the wavelength of the correction light is a wavelength at which absorption by the biological material to be measured is relatively small.

9. The biological material measuring apparatus according to claim 8, wherein
the wavelength of the signal light and the wavelength of the reference light are 8.0 to 10 μm, and
the wavelength of the correction light is 0.8 to 2.5 μm.

10. The biological material measuring apparatus according to claim 9, wherein
the infrared light source includes an infrared light source for signal light configured to radiate the signal light, and an infrared light source for reference light configured to radiate the reference light, and each of the infrared light source for signal light and the infrared light source for reference light is a quantum cascade laser configured to radiate infrared light with a single wavelength.

11. The biological material measuring apparatus according to claim 9, wherein the infrared light source includes an infrared light source for signal light configured to radiate the signal light, and an infrared light source for reference light configured to radiate the reference light, and the infrared light source for signal light and the infrared light source for reference light are a wavelength integrated device including integration of a plurality of quantum cascade lasers configured to radiate infrared light with a single wavelength.

12. The biological material measuring apparatus according to claim 8, wherein the infrared light source includes an infrared light source for the signal light configured to radiate the signal light, and an infrared light source for the reference light configured to radiate the reference light, and each of the infrared light source for signal light and the infrared light source for reference light is a quantum cascade laser configured to radiate infrared light with a single wavelength.

13. The biological material measuring apparatus according to claim 8, wherein the infrared light source includes an infrared light source for signal light configured to radiate the signal light, and an infrared light source for reference light configured to radiate the reference light, and the infrared light source for signal light and the infrared light source for reference light are a wavelength integrated device including integration of a plurality of quantum cascade lasers configured to radiate infrared light with a single wavelength.

14. The biological material measuring apparatus according to claim 8, wherein infrared light with at least one wavelength is absorbed upon occurrence of a plasmon resonance on a surface of a light receiving portion of the infrared photodetector, and the at least one wavelength that has been absorbed corresponds to an absorption wavelength of the biological material to be measured.

15. The biological material measuring apparatus according to claim 8, wherein a surface of a light receiving portion of the infrared photodetector has recesses or projections formed periodically therein, and an outermost surface of the light receiving portion comprises a material that generates a surface plasmon resonance.

16. The biological material measuring apparatus according to claim 15, wherein periods of the recesses or the projections on the surface of the light receiving portion of the infrared photodetector are determined correspondingly to an absorption wavelength of the biological material to be measured.

17. The biological material measuring apparatus according to claim 16, wherein infrared light perpendicularly enters the surface of the light receiving portion of the infrared photodetector.

18. The biological material measuring apparatus according to claim 8, wherein a surface of a light receiving portion of the infrared photodetector is formed of a thin metal film. an insulating film, and metal patches layered in order from inside, and an absorption wavelength is controllable in accordance with a size of the metal patches.

19. The biological material measuring apparatus according to claim 18, wherein the metal patches each have a square shape, and periods at which the metal patches are arranged are greater than an absorption wavelength of the biological material to be measured and are greater than one side of each of the metal patches.

20. The biological material measuring apparatus according to claim 6, wherein the infrared photodetector is configured to selectively detect a specific wavelength.

* * * * *